United States Patent [19]

Muller et al.

[11] Patent Number: 4,743,599

[45] Date of Patent: May 10, 1988

[54] 1,5-BENZOTHIAZEPINE DERIVATIVES AND COMPOSITIONS CONTAINING THEM

[75] Inventors: Jean-Claude Muller, Morsang-sur-Orge; André Dumas, Palaiseau, both of France

[73] Assignee: Synthelabo, Paris, France

[21] Appl. No.: 38,152

[22] Filed: Apr. 14, 1987

[30] Foreign Application Priority Data

Apr. 15, 1986 [FR] France ................................ 86 05346

[51] Int. Cl.$^4$ .................... A61K 31/55; C07D 281/10; C07D 417/06
[52] U.S. Cl. ........................................ 514/211; 540/491
[58] Field of Search .......................... 540/491; 514/211

[56] References Cited

U.S. PATENT DOCUMENTS 3,341,519  9/1967  Krapcho ............................ 540/491
3,562,257  2/1971  Kugita et al. ..................... 540/491

Primary Examiner—Robert T. Bond
Attorney, Agent, or Firm—Fleit, Jacobson, Cohn & Price

[57] ABSTRACT

Compounds which are 1,5-benzothiazepine derivatives of general formula (I)

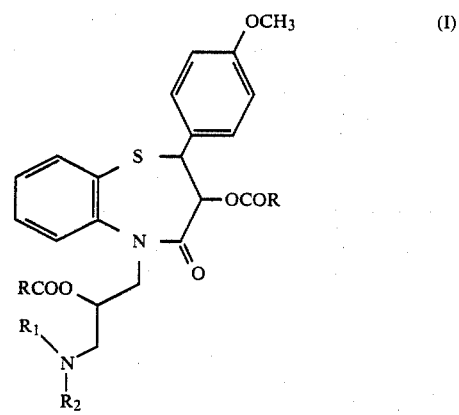

in which R denotes hydrogen or $C_1$–$C_4$ alkyl and $R_1$ and $R_2$ either separately denote $C_1$–$C_4$ alkyl groups or together denote a tetramethylene or pentamethylene group and their acid addition salts are therapeutically active as calcium antagonists.

7 Claims, No Drawings

1,5-BENZOTHIAZEPINE DERIVATIVES AND COMPOSITIONS CONTAINING THEM

The present invention relates to 1,5-benzothiazepine derivatives, their preparation and pharmaceutical compositions containing them.

The compounds of the invention are 1,5-benzothiazopine derivatives of the general formula (I) given in Scheme 1 in which formula R denotes hydrogen or $C_1$–$C_4$ alkyl and $R_1$ and $R_2$ either each separately denote $C_1$–$C_4$ alkyl or together denote a tetramethylene or pentamethylene group, and their pharmacologically acceptable acid addition salts.

The molecule of formula (I) includes several chiral centres, so that the compounds of the invention can take the form of pure enantiomers, diastereoisomers and mixtures thereof. The various optical isomers naturally form part of the invention. The compounds can exist as the free bases of formula (I) or as addition salts with acids.

The compounds of the invention can be prepared according to Scheme 1 below.

A benzothiazepinone of formula (II) is first treated with sodium hydride in a solvent such as dimethyl sulphoxide and then, suitably in the same vessel, the compound obtained is reacted with epichlorohydrin (Z=Cl) or with glycidyl tosylate (Z=tosyloxy), and then with an amine of

Scheme 1

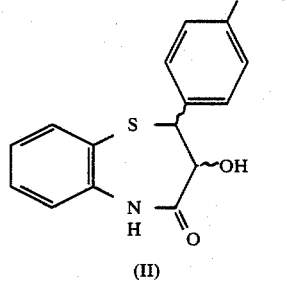

(II)

(1) NaH—DMSO
(2) 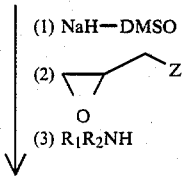
(3) $R_1R_2NH$

-continued
Scheme 1

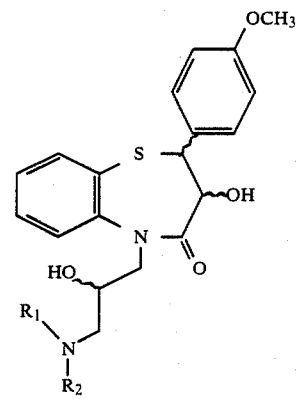

(III)

 RCOX

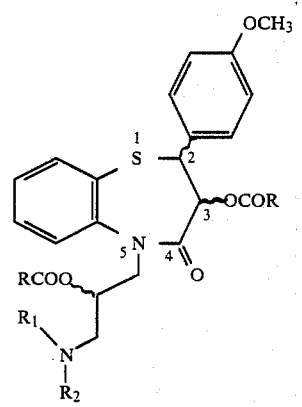

(I)

Scheme 2

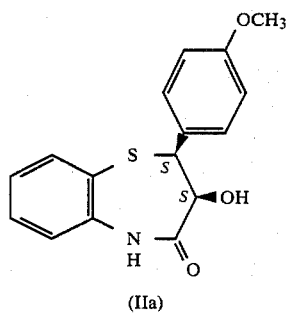

(IIa)

(1) NaH—DMSO
(2) 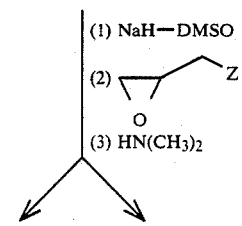
(3) $HN(CH_3)_2$

-continued
Scheme 2

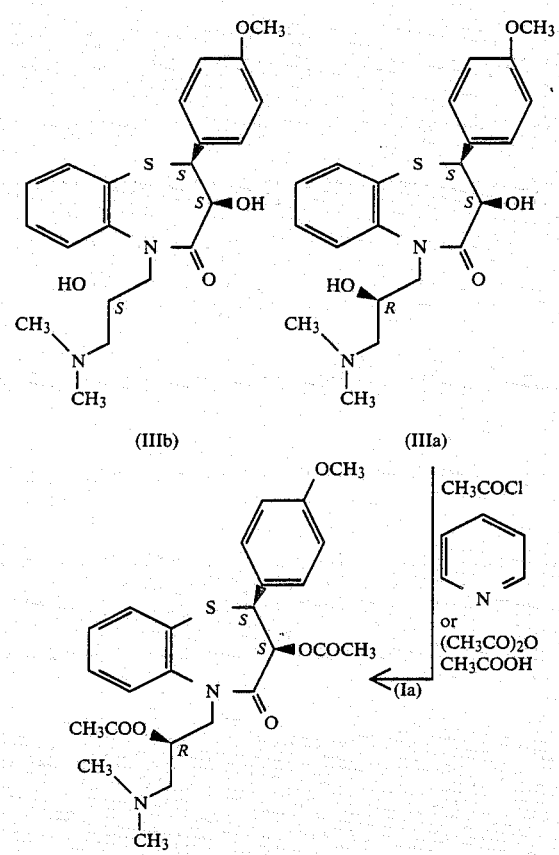

formula HNR₁R₂, R₁ and R₂ being as defined above. The intermediate of formula (III) thereby obtained is a mixture of two diastereoisomers A and B if the starting compound (II) and the glycidyl derivative (epichlorohydrin or glycidyl tosylate) are in the form of racemates. Two mixed diastereoisomers can be separated by fractional crystallization. It is self-evident that it is possible to prepare a single diastereoisomer or a single enantiomer, depending on whether a starting compound (II) and/or a glycidyl derivative is/are used in the form of a pure enantiomer.

The final stage in the process of preparing the derivative of formula (I) consists of an acylation with an acylating agent which is an acid of the formula RCOOH, R being as defined above or an anhydride or halide thereof, suitably in a solvent, such as dichloromethane, and in the presence of a base, such as pyridine or 4-dimethylaminopyridine, to bind the hydrochloric acid liberated. Preferably the acylating agent is the acid halide RCOX. The acid addition salts can be prepared by treating the base of formula (I) with an acid in manner known per se.

Scheme 2 above illustrates the stereospecific preparation of the preferred 1,5-benzothiazepine derivative of formula (I), namely (+)-cis-(2S,3S)-2-(4-methoxyphenyl)-3-acetyloxy-5-[(3R)-3-dimethylamino-2-acetyloxypropyl]-2,3-dihydro-5H-1,5-benzothiazepin-4-one. The formulae (Ia), (IIa), (IIIa) and (IIIb) correspond to the formulae (I), (II) and (III) in which R, R₁ and R₂ each denote a methyl group.

This Scheme 2 also illustrates an acylation stage involving acetylation by means of acetic anhydride and acetic acid.

The Examples which follow illustrate in detail the preparation of a few compounds according to the invention.

The structures of the product obtained were confirmed by microanalyses and IR and NMR spectra.

EXAMPLE 1

3 g (0.062 mole) of 50% strength sodium hydride and 150 ml of dimethyl sulphoxide are introduced under an inert atmosphere into a 500-ml reactor. The mixture is stirred at 70° C. for 1 h and then, after it has been cooled to 20° C., 18.7 g (0.062 mole) of (±)-cis-2-(4-methoxyphenyl)-3-hydroxy-2,3-dihydro-5H-1,5-benzothiazepin-4-one, dissolved in 60 ml of dimethyl sulphoxide, are added. The stirring is maintained at 30° C. for 1 h, the mixture is then cooled to 15° C. and 19.6 ml (0.248 mole) of epichlorohydrin are added. After stirring for 2 h at 20° C., 41 g of dimethylamine are added and the reaction medium is heated to 60° C. for 3 h.

The crude reaction medium is cast into ice-cold bicarbonate solution; the precipitate obtained is filtered off and washed copiously with water. The solid is taken up in dichloromethane, washed with water and dried. After evaporation, 17.5 g of crude mixture are isolated, and this is treated with hydrochloric acid solution in ether and ethanol. 9.7 g of a mixture of diastereoisomers are isolated. By successive crystallizations, either of the diastereoisomers is selectively obtained:

(±)-cis-2-(4-methoxyphenyl)-3-hydroxy-5-(3-dimethylamino-2-hydroxypropyl)-2,3-dihydro-5H-1,5-benzothiazepin-4-one hydrochloride Diastereoisomer A m.p. 213°–217° C.
Diastereoisomer B m.p. 194°–195° C.

4.02 g (0.01 mole) of mixture of diastereoisomers are dissolved in 150 ml of dichloromethane and 15 ml of pyridine. The reaction mixture is cooled in ice and then treated with 3 ml of acetyl chloride. Stirring is maintained overnight and the solvents are then evaporated off under vacuum. The crude product is dissolved in dichloromethane and then washed with saturated sodium bicarbonate solution. After drying and evaporation of the solvent, the residue is treated with ethanolic hydrogen chloride.

After crystallization, 3.94 g of (±)-cis-2-(4-methoxyphenyl)-3-acetyloxy-5-(3-dimethylamino-2-acetyloxypropyl)-2,3-dihydro-5H-1,5-benzothiazepin-4-one hydrochloride (mixture of diastereoisomers) are isolated. M.p. 232° C.

0.8 g (1.82 mole) of the diastereoisomer B is dissolved in a solution of 40 ml of dichloromethane containing 3 ml of pyridine, and the mixture is treated at 0° C. with 0.6 ml of acetyl chloride. The mixture is left standing overnight and the solvent is then evaporated off. The crude residue is taken up in dichloromethane and washed with sodium bicarbonate solution. After drying and evaporation of the solvent, the residue is treated with ethanolic hydrogen chloride.

(±)-cis-2-(4-Methoxyphenyl)-3-acetyloxy-5-(3-dimethylamino-2-acetyloxypropyl)-2,3-dihydro-5H-1,5-benzothiazepin-4-one hydrochloride is quantitatively isolated.

Diastereoisomer B m.p. 145° C.

1.4 g (3.19 mole) of the diastereoisomer A is dissolved in 70 ml of dichloromethane and 5 ml of pyridine and the mixture is treated at 0° C. with 1 ml of acetyl chloride. Stirring is maintained overnight and the solvents are then evaporated off under vacuum. The crude mixture is taken up in dichloromethane and washed with saturated sodium bicarbonate solution. After drying and evaporation of the solvent, the residue is treated in ethanol with one equivalent of fumaric acid.

0.87 g of (±)-cis-2-(4-methoxyphenyl)-3-acetyloxy-5-(3-dimethylamino-2-acetyloxypropyl)-2,3-dihydro-5H-1,5-benzothiazepin-4-one fumarate is isolated.
Diastereoisomer A m.p. 186° C.

EXAMPLE 2

In a similar manner to Example 1, when 3.1 g of (±)-cis-2-(4-methoxyphenyl)-3-hydroxy-2,3-dihydro-5H-1,5-benzothiazepin-4-one are treated with sodium hydride and then with epichlorohydrin (1.6 ml) and pyrrolidine (1.4 ml), 1.4 g of (±)-cis-2-(4-methoxyphenyl)-3-hydroxy-5-(3-pyrrolidinyl-2-hydroxypropyl)-2,3-dihydro-5H-1,5-benzothiazepin-4-one hydrochloride are isolated in the form of a mixture of diastereoisomers.
m.p. 206° C.

In a similar manner to Example 1, acetylation leads to (±)-cis-2-(4-methoxyphenyl)-3-acetyloxy-5-(3-pyrrolidinyl-2-acetyloxypropyl)-2,3-dihydro-5H-1,5-benzothiazepin-4-one hydrochloride in the form of a mixture of diastereoisomers.
M.p. 241° C.

EXAMPLE 3

In a similar manner to Example 1, the treatment of 10 g of (±)-cis-2-(4-methoxyphenyl)-3-hydroxy-2,3-dihydro-5H-1,5-benzothiazepin-4-one with sodium hydride followed, successively, by epichlorohydrin (8 ml) and by isopropylmethylamine (15 ml) leads to 5.77 g of a mixture of diastereoisomers A and B of (±)-cis-2-(4-methoxyphenyl)-3-hydroxy-5-[3-(N-isopropyl-N-methylamino)-2-hydroxypropyl]-2,3-dihydro-5H-1,5-benzothiazepin-4-one in the form of hydrochloride.

By successive crystallizations, the pure diastereoisomers are separated.
Diastereoisomer A m.p. 181° C.

Acetylation of the diastereoisomer A (1.38 g) with acetyl chloride enables 1.21 g of (±)-cis-2-(4-methoxyphenyl)-3-acetyloxy-5-[3-(N-isopropyl-N-methylamino)-2-acetyloxypropyl]-2,3-dihydro-5H-1,5-benzothiazepin-4-one hydrochloride to be isolated.
M.p. 146° C.

EXAMPLE 4

By acetylation of 3.1 g of a mixture of diastereoisomers of (±)-cis-2-(4-methoxyphenyl)-3-hydroxy-5-[3-(N-isopropyl-N-methylamino)-2-hydroxypropyl]-2,3-dihydro-5H-1,5-benzothiazepin-4-one hydrochloride under the conditions described above, 2.9 g of (±)-cis-2-(4-methoxyphenyl)-3-acetyloxy-5-[3-(N-isopropyl-N-methylamino)-2-acetyloxypropyl]-2,3-dihydro-5H-1,5-benzothiazepin-4-one hydrochloride are obtained.
M.p. 152° C.

EXAMPLE 5

1.5 g of mixture of diastereoisomers of (±)-cis-2-(4-methoxyphenyl)-3-hydroxy-5-(3-dimethylamino-2-hydroxypropyl)-2,3-dihydro-5H-1,5-benzothiazepin-4-one hydrochloride in dichloromethane and pyridine is treated at 0° C. with 1 ml of pivaloyl chloride. After isolation and formation of the hydrochloride, 1.6 g of (±)-cis-2-(4-methoxyphenyl)-3-pivaloyloxy-5-(3-dimethylamino-2-pivaloyloxypropyl)-2,3-dihydro-5H-1,5-benzothiazepin-4-one are collected.
M.p. 118° C.

EXAMPLE 6

0.54 g (0.0133 mole) of 50% strength sodium hydride and 55 ml of dimethyl sulphoxide are introduced under an inert atmosphere into a 200-ml reactor. The mixture is stirred vigorously for 1 h at 70° C., and then allowed to return to room temperature. 3.93 g (0.013 mole) (+)-cis-(2S,3S)-2-(4-methoxyphenyl)-3-hydroxy-2,3-dihydro-5H-1,5-benzothiazepin-4-one, dissolved in 12 ml of dimethyl sulphoxide, are added dropwise. The stirring is maintained at 30° C. for 1 h, 2.25 ml (0.024 mole) of (+)-(S)-epichlorohydrin [prepared according to the method of Baldwin, J. Org. Chem 43, 4876 (1978)] are then added, and stirring is continued for 2 h at this temperature. The reaction mixture is treated with 10 g of dimethylamine in dimethyl sulphoxide, heated to 60° C. for 2 hours and then left with its constituents in contact overnight.

The reaction mixture is poured into ice-cold saturated sodium bicarbonate solution, extracted with ether and washed with water. After drying and evaporation, 4.68 g of (+)-cis-(b 2S,3S)-2-(4-methoxyphenyl)-3-hydroxy-5-(3-dimethylamino-2-hydroxypropyl)-2,3-dihydro-5H-1,5-benzothiazepin-4-one are isolated, and this is immediately acetylated with acetyl chloride in pyridine. After extraction and washing, 4.5 g of crude product are isolated, and this is treated with ethanolic hydrogen chloride.

By crystallization in ethyl acetate, 3.55 g of (+)-cis-(2S,3S)-2-(4-methoxyphenyl)-3-acetyloxy-5-[(3R)-3-dimethylamino-2-acetyloxypropyl]-2,3-dihydro-5H-1,5-benzothiazepin-4-one hydrochloride are isolated.
M.p. 140°-142° C. $[\alpha]_D^{20} = +135°$ (c=0.1%, CH$_3$OH).

EXAMPLE 7

0.393 g (0.0082 mole) of 50% strength sodium hydride and 40 ml of dimethyl sulphoxide are introduced under inert atmosphere into a 150-ml reactor. The mixture is stirred for 1 h at 70° C. and cooled to 20° C., and 2.37 g (0.0079 mole) of (+)-cis-(2S,3S)-2-(4-methoxyphenyl)-3-hydroxy-2,3-dihydro-5H-1,5-benzothiazepin-4-one, dissolved in 20 ml of dimethyl sulphoxide, are added. The stirring is maintained at 30° C. for 1 h, the mixture is allowed to cool to 25° C. and 2 g (0.0088 mole) of (−)-(R)-glycidyl tosylate are added in a single portion, and stirring is continued for 2 h 30 min at this temperature. 5 g (0.11 mole) of anhydrous dimethylamine are added, and the mixture is heated to 40° C. for 2 h and left with stirring overnight without heating.

The mixture is poured into ice-cold saturated sodium bicarbonate solution and extracted three times with ether, and the organic phase is washed with water and dried over magnesium sulphate. The ether is evaporated off and the 3.2 g of crude residue are purified by chromatography on a column of silica, eluting with a 90:10:2 dichloromethane/methanol/ammonia solution mixture.

2 g of pure base are obtained, and this is treated with one equivalent of fumaric acid, and, after recrystallization in ethanol, 1.7 g of (+)-cis-(2S,3S)-2-(4-methoxyphenyl)-3-hydroxy-5-[(3R)-3-dimethylamino-2-hydroxypropyl]-2,3-dihydro-5H-1,5-benzothiazepin-4-one fumarate are isolated.
M.p. 158° C. $[\alpha]_D^{20} = +123°$ (c=1%, CH$_3$OH).

1.62 g (0.004 mole) of this compound, in the form of free base, are introduced into a 100-ml reactor equipped with a calcium chloride guard tube and a condenser, 20 ml of acetic acid and 20 ml of acetic anhydride are added and the mixture is heated to 100° C. and with stirring for 6 h.

The mixture is then transferred to a 250-ml evaporator and evaporated under vacuum, adding toluene to carry away the final traces of acetic anhydride. 1.7 g of crude residue are thereby obtained, the hydrochloride of which is prepared by treatment in ethanol with ethereal hydrogen chloride, and this gives 1.7 g of (+)-cis-(2S,3S)-2-(4-methoxyphenyl)-3-acetyloxy-5-[(3R)-3-dimethylamino-2-acetyloxypropyl]-2,3-dihydro-5H-1,5-benzothiazepin-4-one hydrochloride.

M.p. 142° C. $[\alpha]_D^{20} = +131°$ (c=0.1%, $CH_3OH$).

The table on the following page illustrates the structures and physical properties of a few compounds according to the invention.

TABLE

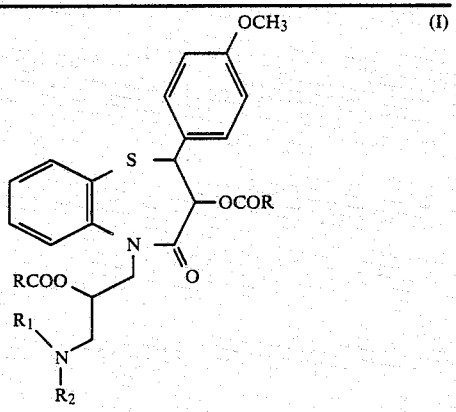

| Compound no. | R | $R_1$ | $R_2$ | Form | Salt* | M.p. (°C.) |
|---|---|---|---|---|---|---|
| 1 (Ex. 1) | $CH_3$ | $CH_3$ | $CH_3$ | (±) A + B | 10 | 232 |
| 2 (Ex. 1) | $CH_3$ | $CH_3$ | $CH_3$ | (±) B | 10 | 145 |
| 3 (Ex. 1) | $CH_3$ | $CH_3$ | $CH_3$ | (±) A | 08 | 186 |
| 4 (Ex. 6–7) | $CH_3$ | $CH_3$ | $CH_3$ | (+) A | 10 | 142 |
| 5 (Ex. 4) | $CH_3$ | $CH_3$ | $CH(CH_3)_2$ | (±) A + B | 10 | 152 |
| 6 (Ex. 3) | $CH_3$ | $CH_3$ | $CH(CH_3)_2$ | (±) A | 10 | 146 |
| 7 (Ex. 5) | $C(CH_3)_3$ | $CH_3$ | $CH_3$ | (±) A + B | 10 | 118 |
| 8 (Ex. 2) | $CH_3$ | | $(CH_2)_4$ | (±) A + B | 10 | 241 |

*08: fumarate
10: hydrochloride

The compounds of the invention were subjected to pharmacological trials which demonstrated their activity as a calcium antagonist.

The experimental protocol used is a variant of that used by Godfraind and Kaba (1969), (Blockade or reversal of the contraction induced by calcium and adrenaline in depolarized arterial smooth muscle, Br. J. Pharmac., 36, 549–560).

The experiments were carried out on sectional lengths of rabbit thoracic aorta. The animals, "Fauves de Bourgogne"0 of average weight 1.5 kg, were sacrificed by cervical dislocation and exsanguination. The thoracic aorta was rapidly removed and placed in an oxygenated Krebs bicarbonate medium (95% $O_2$+5% $CO_2$).

Sectional lengths of aorta approximately 1 cm long were prepared and mounted in 20-ml organ cells containing oxygenated Krebs bicarbonate solution (pH 7.4) at 37° C. Two U-shaped metal hooks having the same length as the sectional lengths were introduced into the bore of the latter. One of the hooks was attached to the base of the cell. The other, connected to an isometric strain gauge (Grass FTO3), enabled the contractile responses of the sectional lengths of aorta to be recorded, via a continuous preamplifier (Grass 7P1), on a recording oscillograph (Grass 79B). This method has the advantage, compared with spiral- or ring-shaped preparations, of preserving more faithfully the structural integrity of the vessels and of recording only the radial component of the contractile responses, which represents the phenomenon which is of interest from a functional standpoint (regulation of the arterial blood pressure). An initial tension of 4 g was applied to the preparations.

Phenoxybenzamine (1 μM) and propranolol (1 μM) were added to the different Krebs media in order to eliminate the contractile responses linked to the activation of the vascular α- and β-adrenergic receptors.

After one hour's stabilization in Krebs bicarbonate medium, the tension applied to the aortas was reduced to 2 g. After a 30-minute waiting period, the preparations were incubated for about 10 minutes in a calcium-free Krebs bicarbonate solution in the presence of EDTA (200 μM) and propranolol (1 μM). This solution was then replaced by a calcium-free depolarizing (potassium-rich) Krebs medium containing propranolol (1 μM). After 5 minutes, a single 1 mM concentration of calcium was added to this solution and a 30-minute stabilization period was observed, this enabling the preparations to attain a stable contraction.

Cumulative doses of the test compounds were then administered every 30 minutes (the time generally needed for obtaining a stable condition) until there was complete disappearance of the contraction induced by 1 mM calcium, or alternatively until a maximal concentration of product of 30 μM was attained. At the end of the experiment, a supramaximal concentration of papaverine (300 μM) was administered in order to determine the maximum possible relaxation of each preparation.

The absolute values (in grams) of the initial contraction (after 1 mM $CaCl_2$) and of the contraction after the different cumulative concentrations of vasodilatory compounds were obtained, for each preparation, by difference with the minimal contraction observed 30 minutes after the final addition of 300 μM papaverine. The percentage decrease in the contraction, relative to the contraction induced by 1 mM calcium, was calculated for each dose of compound and each preparation, and this individual percentage relaxation is averaged $\overline{X} \pm SEM$. The mean values obtained (weighted by the reciprocal of the standard error of the mean) were analysed using a mathematical sigmoid curve model. The molar concentration inducing 50% relaxation of the response to calcium ($EC_{50}$), or alternatively its antilogarithm ($PEC_{50}$), was calculated.

For the compounds of the invention, the $PEC_{50}$ is of the order of 5.8 to 6.

The results of the trials show that the compounds of the invention can be used for the treatment of all diseases in which calcium antagonists can be used, such as angina pectoris, arrhythmia of supraventricular origin, hypertension, cardiomyopathy, myocardial protection of patients at risk of infarction or who have undergone an infarction, cardiac arrest, stroke, mania, migraine.

The compounds of the invention can be presented in any form suitable for oral or parenteral administration, in combination with any suitable excipient, for example in the form of tablets, gelatin capsules, capsules, solutions for oral administration or injectable solutions.

The daily dosage can range from 10 to 400 mg orally and from 1 to 50 mg parenterally.

We claim:

1. A compound, in the form of pure optical isomer, diastereoisomer or mixture thereof having the formula (I)

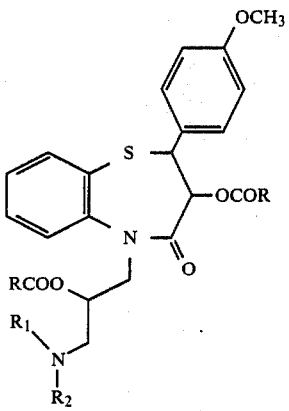

in which R denotes hydrogen or $C_1$–$C_4$ alkyl and $R_1$ and $R_2$, which may be the same or different, each denote $C_1$–$C_4$ alkyl or $R_1$ and $R_2$ together denote a tetramethylene or pentamethylene group, or a pharmacologically acceptable acid addition salt thereof.

2. A compound according to claim 1 wherein R, $R_1$ and $R_2$ each denote methyl.

3. A compound according to claim 1, wherein R is methyl or t-butyl and $R_1$ and $R_2$ either each separately denote methyl or isopropyl or together denote a tetramethylene group.

4. A compound according to claim 1, namely (+)-cis-(2S,3S)-2-(4-methoxyphenyl)-3-acetyloxy-5-[(3R)-3-dimethylamino-2-acetyloxypropyl]-2,3-dihydro-5H-1,5-benzothiazepin-4-one or its hydrochloride or fumarate.

5. A compound of the formula (III)

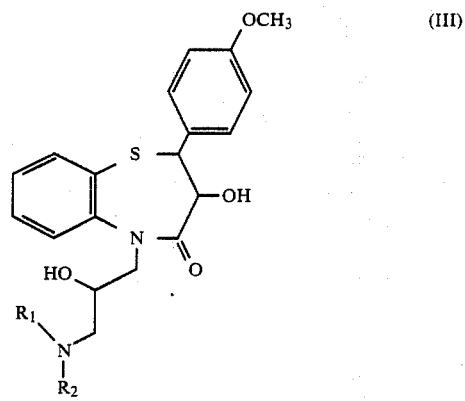

in which $R_1$ and $R_2$, which may be the same or different, each denote $C_1$–$C_4$ alkyl or $R_1$ and $R_2$ together denote a tetramethylene or pentamethylene group, or a pharmacologically acceptable acid addition salt thereof.

6. A compound according to claim 5, namely (+)-cis-(2S,3S)-2-(4-methoxyphenyl)-3-hydroxy-5-[(3R)-3-dimethylamino-2-hydroxypropyl]-2,3-dihydro-5H-1,5-benzothiazepin-4-one.

7. A calcium antagonistic composition which contains, as active ingredient, an effective amount of a compound as claimed in claim 1 in association with a pharmaceutically acceptable excipient.

* * * * *